(12) United States Patent
Kaemmerer

(10) Patent No.: US 7,988,668 B2
(45) Date of Patent: Aug. 2, 2011

(54) MICROSYRINGE FOR PRE-PACKAGED DELIVERY OF PHARMACEUTICALS

(75) Inventor: William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 575 days.

(21) Appl. No.: 11/562,282

(22) Filed: Nov. 21, 2006

(65) Prior Publication Data
US 2008/0119787 A1    May 22, 2008

(51) Int. Cl.
*A61M 37/00* (2006.01)
(52) U.S. Cl. .......................................... 604/150; 604/70
(58) Field of Classification Search .................. 604/110, 604/132, 141, 150, 151, 190, 252
See application file for complete search history.

(56) References Cited

U.S. PATENT DOCUMENTS

| | | | |
|---|---|---|---|
| 4,061,143 A * | 12/1977 | Ishikawa | 604/272 |
| 4,137,917 A * | 2/1979 | Cohen | 604/513 |
| 4,683,195 A | 7/1987 | Mullis et al. | |
| 4,683,202 A | 7/1987 | Mullis | |
| 4,800,159 A | 1/1989 | Mullis et al. | |
| 4,888,829 A | 12/1989 | Kleinerman et al. | |
| 4,965,188 A | 10/1990 | Mullis et al. | |
| 5,236,908 A | 8/1993 | Gruber et al. | |
| 5,286,258 A * | 2/1994 | Haber et al. | 604/90 |
| 5,336,057 A | 8/1994 | Fukuda et al. | |
| 5,354,326 A | 10/1994 | Comben et al. | |
| 5,534,350 A | 7/1996 | Liou | |
| 5,624,803 A | 4/1997 | Noonberg et al. | |
| 5,639,275 A | 6/1997 | Baetge et al. | |
| 5,702,716 A | 12/1997 | Dunn et al. | |
| 5,720,720 A | 2/1998 | Laske et al. | |
| 5,735,814 A | 4/1998 | Elsberry et al. | |
| 5,743,886 A * | 4/1998 | Lynn et al. | 604/191 |
| 5,782,892 A | 7/1998 | Castle et al. | |
| 5,800,390 A | 9/1998 | Hayakawa et al. | |

(Continued)

FOREIGN PATENT DOCUMENTS
DE    19938960    2/2001
(Continued)

OTHER PUBLICATIONS

Aebisher, Trends in Neurosci. 24(9) 553-540 (Sep. 2001).
(Continued)

*Primary Examiner* — Nicholas D Lucchesi
*Assistant Examiner* — Gerald Landry, II
(74) *Attorney, Agent, or Firm* — Mary P. Bauman; Gerard P. Norton; Fox Rothschild LLP

(57) ABSTRACT

A microsyringe includes a body, a barrier movable within the body, and a flow regulator. The body includes a pressurizable chamber, an inlet fluidly connected to the pressurizable chamber, an outlet fluidly connected to the pressurizable chamber, and a cannula fluidly connected to the outlet. The flow regulator is fluidly connected to the cannula to limit the flow of a pharmaceutical through the cannula to a maximum rate. The movable barrier fluidly separates the inlet from the outlet. A pharmaceutical is disposed in a space between the movable barrier and the outlet. The inlet is designed to mechanically and fluidly couple to a hydraulic fluid delivery system. Hydraulic fluid from the inlet pressurizes the chamber, causing the barrier to move and displace the pharmaceutical out of the chamber and into the cannula. The movable barrier may be a piston or a collapsible membrane.

17 Claims, 2 Drawing Sheets

U.S. PATENT DOCUMENTS

| | | | |
|---|---|---|---|
| 5,814,014 A | 9/1998 | Elsberry et al. | |
| 5,840,059 A | 11/1998 | March et al. | |
| 5,846,225 A * | 12/1998 | Rosengart et al. | 604/115 |
| 5,882,561 A | 3/1999 | Barsoum et al. | |
| 5,899,882 A * | 5/1999 | Waksman et al. | 604/103.07 |
| 5,925,310 A | 7/1999 | Nakayama et al. | |
| 5,942,455 A | 8/1999 | Barsoum et al. | |
| 5,968,059 A | 10/1999 | Ellis et al. | |
| 5,997,525 A | 12/1999 | March et al. | |
| 6,042,579 A | 3/2000 | Elsberry et al. | |
| 6,093,180 A | 7/2000 | Elsberry | |
| 6,110,459 A | 8/2000 | Mickle et al. | |
| 6,151,525 A | 11/2000 | Soykan et al. | |
| 6,180,613 B1 | 1/2001 | Kaplitt et al. | |
| 6,187,906 B1 | 2/2001 | Gluckman et al. | |
| 6,231,969 B1 | 5/2001 | Knight et al. | |
| 6,245,884 B1 | 6/2001 | Hook | |
| 6,281,009 B1 | 8/2001 | Boyce | |
| 6,291,243 B1 | 9/2001 | Fogarty et al. | |
| 6,294,202 B1 | 9/2001 | Burns et al. | |
| 6,300,539 B1 | 10/2001 | Morris | |
| 6,309,634 B1 | 10/2001 | Bankiewicz et al. | |
| 6,310,048 B1 | 10/2001 | Kumar | |
| 6,313,268 B1 | 11/2001 | Hook | |
| 6,319,905 B1 | 11/2001 | Mandel et al. | |
| 6,343,233 B1 | 1/2002 | Werner et al. | |
| 6,372,250 B1 | 4/2002 | Pardridge | |
| 6,372,721 B1 | 4/2002 | Neuman et al. | |
| 6,376,471 B1 | 4/2002 | Lawrence, III et al. | |
| 6,394,981 B2 * | 5/2002 | Heruth | 604/140 |
| 6,436,392 B1 | 8/2002 | Engelhardt et al. | |
| 6,436,708 B1 | 8/2002 | Leone et al. | |
| 6,461,989 B1 | 10/2002 | El-Raghy et al. | |
| 6,468,524 B1 | 10/2002 | Chiorini et al. | |
| 6,551,290 B1 | 4/2003 | Elsberry et al. | |
| 6,594,880 B2 | 7/2003 | Elsberry | |
| 6,609,020 B2 | 8/2003 | Gill | |
| 6,632,671 B2 | 10/2003 | Unger | |
| 6,659,995 B1 | 12/2003 | Taheri | |
| 6,793,646 B1 * | 9/2004 | Giambattista et al. | 604/90 |
| 6,802,823 B2 * | 10/2004 | Mason | 604/141 |
| 6,870,030 B2 | 3/2005 | Powell et al. | |
| 6,945,969 B1 | 9/2005 | Morris et al. | |
| 7,320,965 B2 | 1/2008 | Sah et al. | |
| 7,325,572 B2 * | 2/2008 | Schinazi et al. | 138/43 |
| 2001/0027309 A1 | 10/2001 | Elsberry | |
| 2001/0031947 A1 | 10/2001 | Heruth | |
| 2002/0004038 A1 | 1/2002 | Baugh et al. | |
| 2002/0055712 A1 * | 5/2002 | Neracher | 604/143 |
| 2002/0068093 A1 | 6/2002 | Trogolo et al. | |
| 2002/0114780 A1 | 8/2002 | Bankiewicz | |
| 2002/0141980 A1 | 10/2002 | Bankiewicz | |
| 2002/0187127 A1 | 12/2002 | Bankiewicz | |
| 2003/0078229 A1 | 4/2003 | Cooper et al. | |
| 2003/0088236 A1 | 5/2003 | Johnson et al. | |
| 2003/0092003 A1 | 5/2003 | Blatt et al. | |
| 2003/0095958 A1 | 5/2003 | Bhisetti et al. | |
| 2003/0109476 A1 | 6/2003 | Kmiec et al. | |
| 2003/0109834 A2 | 6/2003 | Bitdinger et al. | |
| 2003/0120282 A1 | 6/2003 | Scouten et al. | |
| 2003/0143732 A1 | 7/2003 | Fosnaugh et al. | |
| 2003/0152947 A1 | 8/2003 | Crossman | |
| 2003/0175772 A1 | 9/2003 | Wang | |
| 2003/0190635 A1 | 10/2003 | McSwiggen | |
| 2003/0224512 A1 | 12/2003 | Dobie | |
| 2004/0018520 A1 | 1/2004 | Thompson | |
| 2004/0023390 A1 | 2/2004 | Davidson | |
| 2004/0023855 A1 | 2/2004 | John et al. | |
| 2004/0186422 A1 | 9/2004 | Rioux | |
| 2004/0215164 A1 | 10/2004 | Abott | |
| 2004/0220132 A1 | 11/2004 | Kaemmerer | |
| 2004/0258666 A1 | 12/2004 | Passini | |
| 2004/0259247 A1 | 12/2004 | Tuschl | |
| 2004/0265849 A1 | 12/2004 | Cargill | |
| 2004/0266707 A1 | 12/2004 | Leake | |
| 2005/0032733 A1 | 2/2005 | McSwiggen | |
| 2005/0042646 A1 | 2/2005 | Davidson | |
| 2005/0048641 A1 | 3/2005 | Hildebrand | |
| 2005/0096284 A1 | 5/2005 | McSwiggen | |
| 2005/0119618 A1 * | 6/2005 | Gonnelli | 604/150 |
| 2005/0137134 A1 | 6/2005 | Gill | |
| 2005/0137579 A1 * | 6/2005 | Heruth et al. | 604/536 |
| 2005/0153353 A1 | 7/2005 | Meibohm | |
| 2005/0180955 A1 | 8/2005 | Bankiewicz | |
| 2005/0202075 A1 | 9/2005 | Pardridge | |
| 2005/0209179 A1 | 9/2005 | McSwiggen | |
| 2005/0255086 A1 | 11/2005 | Davidson | |
| 2005/0282198 A1 | 12/2005 | Duff | |
| 2006/0009408 A1 | 1/2006 | Davidson et al. | |
| 2006/0014165 A1 | 1/2006 | Hackonarson | |
| 2006/0041242 A1 | 2/2006 | Stypulkowski | |
| 2006/0052753 A1 * | 3/2006 | Mansouri | 604/187 |
| 2006/0150747 A1 | 7/2006 | Mallett | |
| 2006/0210538 A1 | 9/2006 | Kaplitt et al. | |
| 2006/0224411 A1 | 10/2006 | Chang | |
| 2006/0257912 A1 | 11/2006 | Kaemmerer | |
| 2007/0031844 A1 | 2/2007 | Khvorova et al. | |
| 2007/0088267 A1 * | 4/2007 | Shekalim | 604/134 |
| 2007/0184029 A1 | 8/2007 | Mishra | |
| 2008/0113351 A1 | 5/2008 | Naito | |
| 2009/0022864 A1 | 1/2009 | Steenhof | |

FOREIGN PATENT DOCUMENTS

| | | |
|---|---|---|
| EP | 0532641 B1 | 8/1996 |
| JP | 2004232811 | 8/2004 |
| WO | WO9220400 | 11/1992 |
| WO | WO9323569 | 11/1993 |
| WO | WO9402595 | 2/1994 |
| WO | WO9618736 | 6/1996 |
| WO | WO9740847 | 11/1997 |
| WO | WO9846273 | 10/1998 |
| WO | WO9846740 | 10/1998 |
| WO | WO9939744 | 8/1999 |
| WO | WO9950300 | 10/1999 |
| WO | WO0030567 | 6/2000 |
| WO | WO0064505 | 11/2000 |
| WO | WO0100270 A1 | 1/2001 |
| WO | WO 0100270 A1 | 1/2001 |
| WO | WO0116312 | 3/2001 |
| WO | WO0149844 | 7/2001 |
| WO | WO0160794 | 8/2001 |
| WO | WO0170276 | 9/2001 |
| WO | WO0180840 | 11/2001 |
| WO | WO0191801 | 12/2001 |
| WO | WO0205804 | 1/2002 |
| WO | WO0207810 | 1/2002 |
| WO | WO0222177 | 3/2002 |
| WO | WO03042385 | 5/2003 |
| WO | WO03047676 | 6/2003 |
| WO | WO03053516 | 7/2003 |
| WO | WO03070895 | 8/2003 |
| WO | WO03099298 | 12/2003 |
| WO | WO03102131 | 12/2003 |
| WO | WO2004007718 | 1/2004 |
| WO | WO2004010787 | 2/2004 |
| WO | WO2004013280 | 2/2004 |
| WO | WO2004013355 | 2/2004 |
| WO | WO2004041101 | 5/2004 |
| WO | WO2004047872 | 6/2004 |
| WO | WO2004058940 | 7/2004 |
| WO | WO2004084955 | 10/2004 |
| WO | WO2004098648 | 11/2004 |
| WO | WO2004101063 | 11/2004 |
| WO | WO2005027980 | 3/2005 |
| WO | WO2005045034 | 5/2005 |
| WO | WO2005116204 | 8/2005 |
| WO | WO2005120581 | 12/2005 |
| WO | WO2006022639 | 3/2006 |
| WO | WO2007039721 | 4/2007 |
| WO | WO2007087451 | 8/2007 |
| WO | WO2007139811 | 12/2007 |
| WO | WO2008004260 | 1/2008 |
| WO | WO2008005562 | 1/2008 |
| WO | WO2008021157 | 2/2008 |
| WO | WO2008046273 | 4/2008 |
| WO | WO2008143774 | 11/2008 |

OTHER PUBLICATIONS

Altschul et al., "Gapped BLAST and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 µg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.
Ausubel et al., Eds., Current Protocols in Molecular Biology, vols. 1-3, John Wiley & Sons, Inc., New York, NY, 1994; title page, publisher's page and table of contents only, 14 pgs.
Basi et al., "Antagonistic Effects of β-site Amyloid Precursor Protein-cleaving Enzymes 1 and 2 on β- Amyloid Peptide Production in Cells," J. Bio. Chem., Published, JBC Papers in Press, Jun. 2003; 278(34): 31512-31520.
Bass et al., Nature 411: 428-429 (2001).
Bertrand et al., Biochem Biophys Res Comm 296: 1000-1004 (2002).
Bodendorf et al., J. Neurochem. 80(5), 799-806 (Mar. 2002).
Boillee et al., "Gene therapy for ALS deliver," Trends in Neurosciences, May 2004; 27(5): 235-238.
Bortolin, Susan et al., "Analytical validation of the tag-it high-throughput microsphere-based universal array genotyping platform. Application to the multiplex detection of a panel of thrombophilia-associates single-nucleotide polymorphisms." American Association for Clinical Chemistry vol. 50(11) 2028-2036 (2004).
Brentano et al., P.N.A.S. 89:4099-4103 (1992).
Brummelkamp et al., Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al., Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).
Chi et al., "Genomewide view of gene silencing by small interfering RNAs," Proc. Natl. Acad. Sci. USA, May 2003; 100 (11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; 12(12): 1587-1598.
ElBashir, EMBO J 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behav. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).
Hooper et al., Neuroscience 63, 917-924 (1995).
Hsiao et al, Science 274 99-102(1996).
Huwyler et al., "Brain drug delivery of small molecules using immunoliposomes,"Proc. Natl. Acad., USA, Nov. 1996;93:14164-14169.
Invitrogen, pShooter™ Vector (pCMV/myc © vectors), For the intracellular targeting of recombinant proteins and antibodies, Catalog Nos. V820-20, V821-20, V822-20, V823-20, Version E, copyright 1998-2001, 35 pgs.
Invitrogen, pTRACER™-CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).
Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).
Li et al., Mol. Cell Bio. 22 (5) 1277-1287 (2002).
Lisziewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Luo, Nat. Neurosci. 4, 231-232 (2001).
MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit. # ML022, Rev. Mar. 2, 2005, 5 pgs.
Mirus, TransIT-TKO® Transfection Reagent, Product Nos. MIR 2154, MIR 2150, MIR 2155, MIR 2156, Lit. # ML015, Rev. Jul. 2004, 6 pgs.
Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al., Proc. Nat. Acad. Sci. 93, 11382-11388 (Oct. 1996).
National Center for Biotechnology Information, National Library of Medicine, National Institutes of Health, "What does NCBI do?" [online]. Bethesda, MD [retrieved on Dec. 5, 2005], Revised Dec. 2005. Retrieved from the Internet: <URL:http://www.ncbi.nlm.nih.gov>; 2 pgs.
National Center for Biotechnology Information, National Library of Medicine, National Institutes of Health, GenBank Locus AF163864, Accession No. AF163864, "*Homo sapiens* SNCA isoform (SNCA) gene, complete cds, alternatively spliced," [online]. Bethesda, MD [retrieved on Jun. 21, 2004]. Retrieved from the Internet: <URL:http://www.ncbi.nlm.nih.gov/entrez/viewer.fcgi?db=nucleotide&val=11118351>; 43 pgs.

National Center for Biotechnology Information, National Library of Medicine, National Institutes of Health, GenBank Locus AF163865, Accession No. AF163865, "*Mus musculus* alpha-synuclein (Snca) gene, complete cds," [online]. Bethesda, MD [retrieved on Jun. 21, 2004]. Retrieved from the Internet:<URL:http://www.ncbi.nlm.nih.gov/entrez/viewer.fcgi?db=nucleotide&val=11118354>; 33 pgs.

National Center for Biotechnology Information, National Library of Medicine, National Institutes of Health, GenBank Locus AH003045, Accession No. AH003045, "*Homo sapiens* huntingtin (HD) gene, exon 1," [online]. Bethesda, MD [retrieved on Mar. 5, 2009]. Retrieved from the Internet:<URL:http://www.ncbi.nlm.nih.gov/entrez/viewer.fcgi?db=nucleotide&val=663286>; 42 pgs.

National Center for Biotechnology Information, National Library of Medicine, National Institutes of Health, GenBank Locus NM_000027, Accession No. NM_000027, "*Homo sapiens* aspartylglucosaminidase (AGA), mRNA," [online]. Bethesda, MD [retrieved on Mar. 5, 2009]. Retrieved from the Internet:<URL:http://www.ncbi.nih.gov/entrez/viewer.fcgi?db=nucleotide&val=32313568>; 4 pgs.

National Center for Biotechnology Information, National Library of Medicine, National Institutes of Health, GenBank Locus NM_000046, Accession No. NM_000046, "*Homo sapiens* arylsulfatase B (ARSB), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=38569404>; 4 pgs.

National Center for Biotechnology Information, National Library of Medicine, National Institutes of Health, GenBank Locus NM_000049, Accession No. NM_000049, "*Homo sapiens* aspartoacylase (aminoacylase 1, Canavan disease) (ASPA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557334>; 4 pgs.

National Center for Biotechnology Information, National Library of Medicine, National Institutes of Health, GenBank Locus NM_000147, Accession No. NM_000147, "*Homo sapiens* fucosidase, alpha-L1, tissue (FUCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24475878>; 3 pgs.

National Center for Biotechnology Information, National Library of Medicine, National Institutes of Health, GenBank Locus NM_000152, Accession No. NM_000152, "*Homo sapiens* glucosidase, alpha; acid (Pompe disease, glycogen storage disease type II) (GAA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=11496988>; 4 pgs.

National Center for Biotechnology Information, National Library of Medicine, National Institutes of Health, GenBank Locus NM_000153, Accession No. NM_000153, "*Homo sapiens* galactosylceramidase (Krabbe disease) (GALC), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557612>; 5 pgs.

National Center for Biotechnology Information, National Library of Medicine, National Institutes of Health, GenBank Locus NM_000157, Accession No. NM_000157, "*Homo sapiens* glucosidase, beta; acid (includes glucosylceramidase) (GBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4503934>; 7 pgs.

National Center for Biotechnology Information, National Library of Medicine, National Institutes of Health, GenBank Locus NM_000158, Accession No. NM_000158, "*Homo sapiens* glucan (1, 4-alpha-), branching enzyme 1 (glucogen branching enzyme, Andersen disease, glycogen storage disease trype (IV)(GBE1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557618>; 2 pgs.

National Center for Biotechnology Information, National Library of Medicine, National Institutes of Health, GenBank Locus NM_000181, Accession No. NM_000181, "*Homo sapiens* glucuronidase, beta (GUSB), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504222>; 4 pgs.

National Center for Biotechnology Information, National Library of Medicine, National Institutes of Health, GenBank Locus NM_000199, Accession No. NM_000199, "*Homo sapiens* N-sulfoglucosamine sulfohydrolase (sulfamidase) (SGSH), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=31543619>; 3 pgs.

National Center for Biotechnology Information, National Library of Medicine, National Institutes of Health, GenBank Locus NM_000202, Accession No. NM_000202, "*Homo sapiens* iduronate 2-sulfatase (Hunter syndrome)(ID), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=5360215>; 8 pgs.

National Center for Biotechnology Information, National Library of Medicine, National Institutes of Health, GenBank Locus NM_000203, Accession No. NM_000203, "*Homo sapiens* iduronidase, alpha-L-(IDUA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40354208>; 6 pgs.

National Center for Biotechnology Information, National Library of Medicine, National Institutes of Health, GenBank Locus NM_000235, Accession No. NM_000235, "*Homo sapiens* lipase A, lysosomal acid, cholesterol esterase (Wolman disease) (LIPA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557720>; 4 pgs.

National Center for Biotechnology Information, National Library of Medicine, National Institutes of Health, GenBank Locus NM_000262, Accession No. NM_000262, "*Homo sapiens* N-acetylgalactosaminidase, alpha- (NAGA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557780>; 4 pgs.

National Center for Biotechnology Information, National Library of Medicine, National Institutes of Health, GenBank Locus NM_000263, Accession No. NM_000263, "*Homo sapiens* N-acetylglucosaminidase, alpha-(Sanfilippo disease) (IIIB)(NAGLU), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40548380>; 4 pgs.

National Center for Biotechnology Information, National Library of Medicine, National Institutes of Health, GenBank Locus NM_000310, Accession No. NM_000310, "*Homo sapiens* palmitoyl-protein thioesterase 1 (ceroid-lipofuscinosis, neuronal 1, infantile) (PPT1), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4506030>; 4 pgs.

National Center for Biotechnology Information, National Library of Medicine, National Institutes of Health, GenBank Locus NM_000332, Accession No. NM_000332, "*Homo sapiens* spinocerebellar ataxia 1 (olivopontocerebellar ataxia 1, autosomal dominant, ataxin 1) (SCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4506792>; 7 pgs.

National Center for Biotechnology Information, National Library of Medicine, National Institutes of Health, GenBank Locus NM_000345, Accession No. NM_000345, "*Homo sapiens* synuclein, alpha (nonA4 component of amyloid precursor) (SNCA), transcript variant NACP140, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806896>; 6 pgs.

National Center for Biotechnology Information, National Library of Medicine, National Institutes of Health, GenBank Locus NM_000404, Accession No. NM_000404, "*Homo sapiens* glactosidase, beta 1 (GLB1), transcript variant 179423, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=10834965>; 5 pgs.

National Center for Biotechnology Information, National Library of Medicine, National Institutes of Health, GenBank Locus NM_000434, Accession No. NM_000434, "*Homo sapiens* sialidase 1 (lysosomal sialidase)(NEU1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40806202>; 5 pgs.

National Center for Biotechnology Information, National Library of Medicine, National Institutes of Health, GenBank Locus NM_000487, Accession No. NM_000487, "*Homo sapiens* arysulfatase A (ARSA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=7262293>; 4 pgs.

National Center for Biotechnology Information, National Library of Medicine, National Institutes of Health, GenBank Locus NM_000512, Accession No. NM_000512, "*Homo sapiens* galactosamine (N-acetyl)-6-sulfate sulfatase (Morquio syndrome, mucopolysaccharidosis type IVA), (GALNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=9945384>; 4 pgs.

National Center for Biotechnology Information, National Library of Medicine, National Institutes of Health, GenBank Locus NM_000520, Accession No. NM_000520, "*Homo sapiens* hexosaminidase A (alpha polypeptide) (HEXA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13128865>; 5 pgs.

National Center for Biotechnology Information, National Library of Medicine, National Institutes of Health, GenBank Locus NM_000521, Accession No. NM_000521, "*Homo sapiens* hexosaminidase B (beta polypeptide) (HEXB), mRNA," [online]. Bethesda, MD [retrieved on Mar. 5, 2009]. Retrieved from the Internet:<URL:http://www.ncbi.nlm.nih.gov/entrez/viewer.fcgi=db=nucleotide&val=13128866>; 6 pgs.

National Center for Biotechnology Information, National Library of Medicine, National Institutes of Health, GenBank Locus NM_000528, Accession No. NM_000528, "*Homo sapiens* mannosidase, alpha, class 2B, member 1 (MAN2B1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=10834967>; 4 pgs.

National Center for Biotechnology Information, National Library of Medicine, National Institutes of Health, GenBank Locus NM_000543, Accession No. NM_000543, "*Homo sapiens* sphingomyelin phosphodiesterase 1 acid lysosomal (acid sphingomyelinase) (SMPD1), mRNA," [online]. Bethesda, MD [retrieved on Mar. 5, 2009]. Retrieved from the Internet:<URL:http://ncbi.nlm.nih.gov/entrez/viewer.fcgi?db=nucleotide&val=40254417>; 5 pgs.

National Center for Biotechnology Information, National Library of Medicine, National Institutes of Health, GenBank Locus NM_002076, Accession No. NM_002076, "*Homo sapiens* glucosamine (N-acetyl)-6-sulfatase (Sanfilippo disease)(IIID)(GNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=42490755>; 7 pgs.

National Center for Biotechnology Information, National Library of Medicine, National Institutes of Health, GenBank Locus NM_002778, Accession No. NM_0002778, Accession No. NM_000169, "*Homo sapiens* glactosidase, alpha (GLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504008>; 4 pgs.

National Center for Biotechnology Information, National Library of Medicine, National Institutes of Health, GenBank Locus NM_002778, Accession No. NM_002778, "*Homo sapiens* prosaposin (variant Gaucher disease and variant metachromatic leukodystrophy) (PSAP), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=11386146>; 8 pgs.

National Center for Biotechnology Information, National Library of Medicine, National Institutes of Health, GenBank Locus NM_004315, Accession No. NM_004315, "*Homo sapiens* N-acylsphingosine amidohydrolase (acid ceramidase) 1 (ASAHI), transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=30089929>; 5 pgs.

National Center for Biotechnology Information, National Library of Medicine, National Institutes of Health, GenBank Locus NM_004993, Accession No. NM_004993, "*Homo sapiens* Machado-Joseph disease (spinocerebellar ataxia 3, olivopontocerebellar ataxia 3, autosomal dominant, ataxin 3) (MJD), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518018>; 9 pgs.

National Center for Biotechnology Information, National Library of Medicine, National Institutes of Health, GenBank Locus NM_005908, Accession No. NM_005908, "*Homo sapiens* mannosidase, beta A, lysosomal (MANBA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=24797157>; 4 pgs.

National Center for Biotechnology Information, National Library of Medicine, National Institutes of Health, GenBank Locus NM_007308, Accession No. NM_007308, "*Homo sapiens* synuclein, alpha (nonA4 component of amyloid precursor) (SNCA), transcript variant NACP112, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806897>; 5 pgs.

National Center for Biotechnology Information, National Library of Medicine, National Institutes of Health, GenBank Locus NM_009124, Accession No. NM_009124, "DEFINITION," [online]. Bethesda, MD [retrieved on Mar. 5, 2009]. Retrieved from the Internet:<URL:http://www.ncbi.nlm.nih.gov/entrez/viewer.fcgi?db=nucleotide&val=33636695>; 5 pgs.

National Center for Biotechnology Information, National Library of Medicine, National Institutes of Health, GenBank Locus NM_011792, Accession No. NM_011792, Version NM_011792.2, "*Mus musculus* beta-site APP cleaving enzyme 1 (Bace 1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=31981411>; 5 pgs.

National Center for Biotechnology Information, National Library of Medicine, National Institutes of Health, GenBank Locus NM_011792.2, Accession No. NM_011792, "*Mus musculus* beta-site APP cleaving enzyme (Bace), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6857758>; 4 pgs.

National Center for Biotechnology Information, National Library of Medicine, National Institutes of Health, GenBank Locus NM_012104, Accession No. NM_012104, "*Homo sapiens* beta-site APP-cleaving enzyme 1 (BACE1), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255011>; 8 pgs.

National Center for Biotechnology Information, National Library of Medicine, National Institutes of Health, GenBank Locus NM_012104, Accession No. NM_012104, Version NM_012104.2, "*Homo sapiens* beta-site APP-cleaving enzyme (BACE), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040369>; 10 pgs.

National Center for Biotechnology Information, National Library of Medicine, National Institutes of Health, GenBank Locus NM_013995, Accession No. NM_013995, "*Homo sapiens* lysosomal-associated membrane protein 2 (LAMP2), transcript variant LAMP2B, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=7669502>; 6 pgs.

National Center for Biotechnology Information, National Library of Medicine, National Institutes of Health, GenBank Locus NM_030660, Accession No. NM_030660, "*Homo sapiens* Machado-Joseph disease (spinocerebellar ataxia 3, olivopontocerebellar ataxia 3, autosomal dominant, ataxin 3) (MJD), transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518012>; 8 pgs.

National Center for Biotechnology Information, National Library of Medicine, National Institutes of Health, GenBank Locus NM_032520, Accession No. NM_032520, "*Homo sapiens* N-acetylglucosamine-1-phosphotransferase, gamma subunit (GNPTAG), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=42476109>; 5 pgs.

National Center for Biotechnology Information, National Library of Medicine, National Institutes of Health, GenBank Locus NM_138971, Accession No. NM_138971, "*Homo sapiens* beta-site APP-cleaving enzyme 1 (BACE1), transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255012>; 8 pgs.

National Center for Biotechnology Information, National Library of Medicine, National Institutes of Health, GenBank Locus NM_138971, Accession No. NM_138971, Version NM_138971.1, "*Homo sapiens* beta-site APP-cleaving enzyme (BACE), transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040363>; 10 pgs.

National Center for Biotechnology Information, National Library of Medicine, National Institutes of Health, GenBank Locus NM_138972, Accession No. NM_138972, "*Homo sapiens* beta-site APP-cleaving enzyme 1 (BACE1), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255013>; 8 pgs.

National Center for Biotechnology Information, National Library of Medicine, National Institutes of Health, GenBank Locus NM_138972, Accession No. NM_138972, Version NM_138972.1, "*Homo sapiens* beta-site APP-cleaving enzyme (BACE), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040365>; 10 pgs.

National Center for Biotechnology Information, National Library of Medicine, National Institutes of Health, GenBank Locus NM_138973, Accession No. NM_138973, "*Homo sapiens* beta-site APP-cleaving enzyme 1 (BACE1), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255014>; 8 pgs.

National Center for Biotechnology Information, National Library of Medicine, National Institutes of Health, GenBank Locus NM_138973, Accession No. NM_138973, Version NM_138973.1, "*Homo sapiens* beta-site APP-cleaving enzyme (BACE), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040367>; 10 pgs.

National Center for Biotechnology Information, National Library of Medicine, National Institutes of Health, GenBank Locus U24233, Accession No. U24233, "*Mus musculus* huntingtin (Hd) mRNA, complete cds," [online]. Bethesda, MD [retrieved on Mar. 5, 2009]. Retrieved from the Internet:<URL:http://www.ncbi.nlm.nih.gov/entrez/viewer.fcgi?db=nucleotide&val=902003>; 5 pgs.

National Center for Biotechnology Information, National Library of Medicine, National Institutes of Health, GenBank Locus XM_032588, Accession No. XM_032588, "*Homo sapiens* dentatorubral-pallidoluysian atrophy (artrophin-1) (DRPLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=20555988>; 3 pgs.

National Center for Biotechnology Information, National Library of Medicine, National Institutes of Health, GenBank Locus XM_132846, Accession No. XM_132846, "*Mus musculus* dentatorubral pallidoluysian atrophy (Drpla) mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=20832263>; 3 pgs.

Noonberg et al., Nucl. Acid Res. 22(14) 2830-2836 (1994).
Noordmans et al., Soc. Neurosci. Abstr. 27, Program 572.14 (2001).
Ohkawa Nucl. Acid. Symp. Ser. 27, 15-16 (1992).
Ohno et al., "BACEI Deficiency Rescues Memory Deficits and Cholinergic Dysfunction in a Mouse Model of Alzheimer's Disease," Neuron, Jan. 2004; 4I: 27-33.
Ojwang et al., Proc. Nat. Acad. Sci. 89 10802-10806.
Paxinos et al The Mouse Brain in Stereotactic Coordinates, Acad. Press 2nd Ed. (2001).
Potter, N. T. et al., "Technical standards and guidelines for huntington disease testing," Genetics in Medicine 6:61-65 (2004).
Promega Corporation, T4 DNA Ligase Blue/White Cloning Qualified, Part# 9PIM180, Revised Apr. 2005, 2 pgs.
Promega Corporation, T4 DNA Polymerase(a) , Part# 9PIM421, Revised May 2004, 2 pgs.
Qiagen, Qiaex II Handbook, Feb. 1999, 24 pgs.
Qiagen, Rneasy Mini Handbook, 3rd Edition, Jun. 2001, 116 pgs.
R&D Systems, β-Secretase Activity Kit, Catalog No. FP002, Aug. 2002, 2 pgs.
Roberds et al., "BACE knockout mice are healthy despite lacking the primary β-secretase activity in brain: implications for Alzheimer's disease therapeutics," Human Molecular Genetics, Jun. 2001; 10(12): 1317-1324.
Ryu, Biomaterials 26: 319-326 (2005).
Salehi et al., J. Neural Transm. 106 955-986 (1999).
Sapru et al., Annual Meeting Soc. Neurosci. Abstract 297.9, XP001204566 (2003).
Sarver et al., Science 247, 1222-1225 (1990).
Scanlon et al., Proc. Nat. Acad. Sci. 88, 10591-10595 (1995).
Schenk, "Amyloid-β immunotherapy for Alzheimer's disease: the end of the beginning," Nature Reviews—Neuroscience, Oct. 2002; 3: 824-828.
Scherr et al., Cell Cycle 2(3) 251-257 (2003).
Serra et at., Medical Image Analysis 1(4) 317-329 (1996).
Singer et al., Nat. Neurosci. 8(10) 1343-1349 (ePub Aug. 28, 2005).
Stackman et al., Experimental Neurology 184, 510-520 (2003).
Strategene, AAV Helper-Free System, Instruction Manual, Catalog #240071, #240074, #240075, Revision #084007i, Aug. 2004, 50 pgs.
Strategene, pBluescript® II Phagemid Vectors, Instruction Manual, Catalog #212205, #212206, #212207, #212208, Revision #083001m, Aug. 2003, 35 pgs.
Sullenger, Science 262, p. 1566 (Dec. 3, 1993).
Taira et al., Nucl. Acid. Res. 19(19) 5125-5130 (1991).
Thompson et al., Nucl. Acid. Res. 23(12), 2259 (1995).
Timson et al., Biochem J 363:515-520 (2002).
Tuscjl Lab, "The siRNA user guide," Revised May 2004, [online]. Retrieved on Nov. 29, 2005. Retrieved from the Internet:<URL:rockefeller.edu/labheads/tuschl/sirna.html>; 6 pgs.
Valbonesi et al., Ttransf. And Apheresis Sci. 30: 153-156 (2004).
Van Bilsen et al., "Identification and allele-specific silencing of the mutant huntingtin allele in Huntington's disease patient-derived fibroblasts," Human Gene Therapy, vol. 19, pp. 710-718 (2008).
Vassar et al., Science 286 735-741 (1999).

Ventura et al., Nucl. Acid. Res. 21(14) 3249-3255 (1993).
Vickers, Journal of Bio. Chemistry, vol. 278, No. 9 7108-7118 (2003).
Watanabe et al., J. Mol. Cel. Card. 37 (3) 691-698 (2004).
Weerasinghe et al., J. Virol. 65(10), 5531-3334 (1991).
Whitesell et al., Proc. Nat. Acad. Sci. 90: 4665-4669 (1993).
Xia et al., Nat. Biotech. 20, 1006-1010 (2002).
Xia et al., Nat. Med. 10(8) 816-820 (2004).
Yamamoto et al., Cell 101, 57-66 (2000).
Yu et al., Proc. Nat. Acad. Sci. 90 6340-6344 (1993).
Yu et al., Proc. Nat. Acad. Sci. 99 6047-6052 (2002).
Zhang et al., "Global Non-Viral Gene Transfer to the Primate Brain Following Intravenous Administration," Molecular Therapy, Jan. 2003; 7(1): 11-18.
Zhang et al., "In vivo knockdown of gene expression in brain cancer with intravenous RNAi in adult rats," J. Gene Med., 2003; 5:1039-1045; published online Aug. 4, 2003.
Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.
Zhang et al., 1996 J. Mol. Neurosci. 7: 13-28 (1996).
Zhao et al., J. Biol. Chem. 271(49), 31407-31411 (Dec. 1996).
Zlokovic et al., Neurosurgery 40 805-813 (1997).

* cited by examiner

MICROSYRINGE FOR PRE-PACKAGED DELIVERY OF PHARMACEUTICALS

FIELD OF THE INVENTION

The present invention relates to a microsyringe. More particularly, the present invention discloses a microsyringe pre-filled with a pharmaceutical and designed to provide controlled delivery of small amounts of the pharmaceutical at slow delivery rates.

BACKGROUND OF THE INVENTION

Today, therapies exist that involve the administration at precisely defined locations of very small amounts of a pharmaceutical over the course of minutes or even hours. These therapies include, for example, viral vectors for gene therapy, or protein suppression therapies. As some of these pharmaceuticals can be extremely expensive, waste of the pharmaceutical is to be minimized. Waste of the pharmaceutical may occur, for example, from dead space within the delivery system, such as the volumes inherent in catheters, needles, syringes and the like. For practical reasons, such as when delivering the pharmaceutical to brain tissue, the pharmaceutical cannot be diluted up to higher volumes. Hence, precisely controlled delivery of small amounts of a pharmaceutical with minimal waste is greatly desired for such therapies.

SUMMARY OF THE INVENTION

One aspect of the invention discloses a microsyringe adapted to provide controlled delivery of small amounts of a pharmaceutical. The microsyringe includes a body, a barrier movably disposed within the body, and a flow regulator. The body includes a pressurizable chamber, an inlet fluidly connected to the pressurizable chamber, an outlet fluidly connected to the pressurizable chamber, and a cannula fluidly connected to the outlet. The flow regulator is fluidly connected to the cannula to limit the flow of a pharmaceutical through the cannula to a maximum rate. The cannula may be a catheter, hypodermic needle or the like. The movable barrier fluidly separates the inlet from the outlet. A pharmaceutical is disposed in a space between the movable barrier and the outlet. The inlet is designed to mechanically and fluidly couple to a hydraulic fluid delivery system. Hydraulic fluid from the inlet pressurizes the chamber, causing the barrier to move and displace the pharmaceutical out of the chamber and into the cannula. The flow regulator ensures that the flow rate of the pharmaceutical through the cannula is not excessive.

In one embodiment, during manufacture of the microsyringe, the microsyringe may be pre-loaded with the pharmaceutical. The body may be formed of a material capable of withstanding temperatures of at least $-80°$ C. so as to conform to the storage protocols of the pharmaceutical.

In certain embodiments, the movable barrier may be a piston slidably disposed within the pressurizable chamber. In other embodiments, the movable barrier may be a collapsible membrane disposed within the pressurizable chamber.

DETAILED DESCRIPTION

Figure 1:
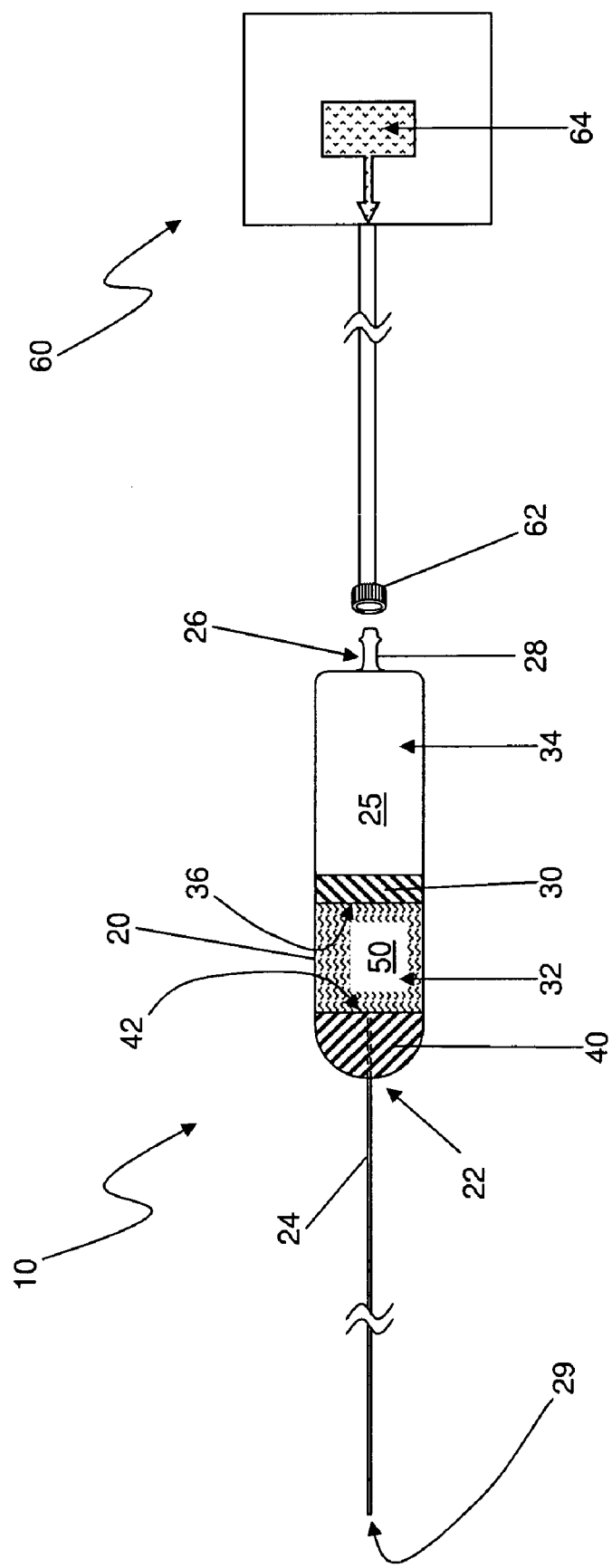
FIG. 1 is a side view of a first embodiment microsyringe.
Figure 2:
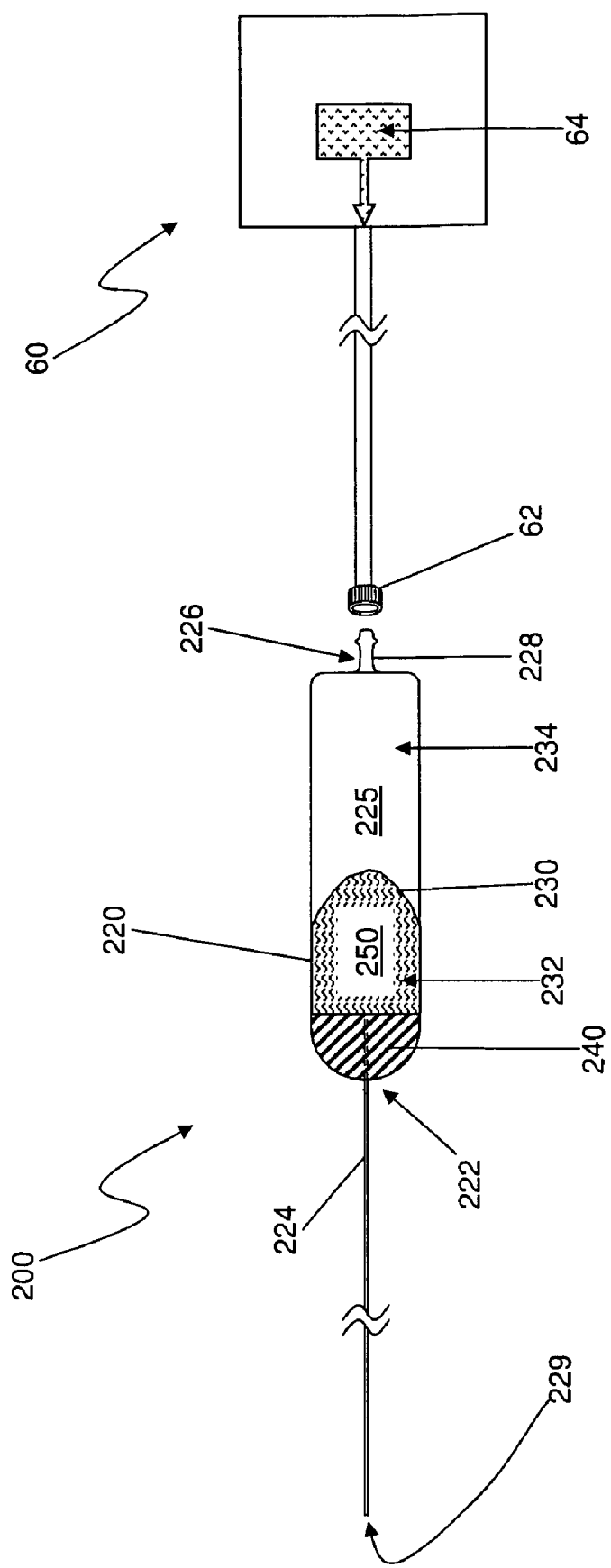
FIG. 2 is a side view of a second embodiment microsyringe.

A first embodiment microsyringe 10 is depicted in FIG. 1. The microsyringe 10 comprises a body 20, a barrier 30 and a flow regulator 40. In one embodiment, the microsyringe is provided to the end-user with the all the parts already assembled (including both the body and the delivery cannula) and the body pre-filled with the pharmaceutical 50. The microsyringe 10 is designed to provide for the administration of a pharmaceutical 50 to a patient in need thereof; the pharmaceutical 50 may be, for example, a viral vector for gene-based therapies. In one embodiment, the vector is stored and transported in a frozen state; even upon thawing at the point of use, the fluid won't leak out (with normal handling) to any significant amount because of the small amount of fluid involved. With microliter volumes and small diameters of fluid pathways, the surface tension of the fluid is sufficient to keep the fluid from leaking out so long as the delivery tip does not come in contact with a material that would draw the fluid out by "capillary" action, such as a paper towel. A detachable connection may (e.g., a threaded connection) be used so that the cannula 24 is not integral with the chamber 25.

Because the microsyringe 10 is designed for the administration of the pharmaceutical 50, and as it is further envisioned that the microsyringe 10 will be provided to a physician pre-packaged with the pharmaceutical 50, the body 20 is preferably made from a material that can both withstand the temperatures commonly employed to store and preserve the pharmaceutical 50, and which is compatible with the pharmaceutical 50. Compatibility indicates that the materials used to form the microsyringe 10, and in particular the body 20, do not adversely affect the therapeutic efficacy of the pharmaceutical 50 over the expected shelf-life of the microsyringe 10. Because temperatures as low as $-80°$ C. may be used to store and preserve the pharmaceutical 50, it may be desirable that the material used to form the body 20 be able to withstand temperatures of at least $-80°$ C.; that is, when removed from cold storage, the material should not subsequently fail when the microsyringe 10 is used, or cause leakage, waste or contamination of the pharmaceutical 50. Exemplary materials suitable for the body 20 include, but are not limited to, polyethylene or polypropylene. Exemplary methods for manufacturing of the body 20 include molding of the body in two halves that are later connected together by a threaded connection, where each half is formed by extrusion blow molding, injection blow molding, or stretch blow molding.

In certain embodiments, the body 20 defines a pressurizable chamber 25 having an inlet 26 and an outlet 22. The pressurizable chamber 25 may, for example, have an internal volume of 0.050-0.500 $cm^3$. Both the inlet 26 and the outlet 22 are fluidly connected to the pressurizable chamber 25. Inlet 26 may include a quick connect/disconnect fitting 28 designed to mechanically and fluidly connect to a corresponding quick connect/disconnect mating 62 of a hydraulic fluid delivery system 60. Such hydraulic mating fixtures are known, and may include, for example and without limitation, the hydraulic coupler set part number 9A2 AZ025 001 manufactured by Kent Systems, LLC, Loveland, Colo., USA. The corresponding mating connections 28, 62 should provide a fluid-tight seal that enables the hydraulic fluid delivery system 60 to provide hydraulic fluid 64 to the pressurizable chamber 25 without loss of pressure. Additionally, the body 20 defines a cannula 24 that is fluidly connected to the outlet 22. The cannula 24 is preferably a catheter, but may also be a hypodermic needle or the like. The cannula 24 may have a length of about 5 cm to about 20 cm. The cannula 24 may have an external diameter of 0.20 mm to 1.30 mm, and an internal diameter of about 0.10 mm to about 0.90 mm. These dimensions are comparable to a syringe needle of gauge 33 to gauge 18. A person of the ordinary skill in the art will appreciate that the fluid pressure needed to move the pharmaceutical 50 through the cannula at the desired flow rates (ranging from 0.10 to 5.0 microliters per minute) is so small that pressure rating of the material thickness of cannula 24 is not an engineering constraint. For purposes of the following disclosure, it is assumed that cannula 24 is a catheter, but it should be understood that microsyringes of the instant invention are not so limited.

In a preferred embodiment, the flow regulator 40 is disposed within the pressurizable chamber 25 and fluidly connected to the catheter 24 via the outlet 22. Hence, any pharmaceutical 50 that would pass through the outlet 22 into the catheter 24 must first pass through the flow regulator 40. As known to those skilled in the art, the flow regulator may be comprised of a tortuous fluid path, such as disclosed, for example, in U.S. Pat. No. 5,993,414, or it may comprise a deflectable membrane as disclosed, for example, in U.S. Pat. No. 6,203,523 and U.S. Pat. No. 6,878,135. In the preferred embodiment of the subject invention, the flow regulator is a separate device inserted into the body 20 and connected to the catheter 24 via outlet 22 at the time the body is assembled, prior to the filling of pharmaceutical reservoir chamber 32 with the deliverable pharmaceutical. The flow regulator 40 prevents the flow rate of the pharmaceutical 50 in the catheter 24 from exceeding a predetermined maximum rate. Thus, the flow regulator 40 thereby prevents the delivery rate of the pharmaceutical 50 to a patient from exceeding the maximum rate. The maximum flow rate will, of course, depend upon the type of pharmaceutical 50 that is being delivered to the patient, and the treatment regimen. Exemplary maximum rates may range from about 0.10 to about 5.0 microliters per minute. For example, if the pharmaceutical 50 is a solution of adeno-associated viral vector particles in saline, the maximum flow rate for a given therapy delivery to a given patient may be 1.0 microliters per minute. Suitable flow regulators 40 are described, without limitation in U.S. Pat. Nos. 5,993,414, 6,203,523 and 6,878,135, incorporated herein by reference in their entireties. For example, the flow regulator 40 may comprise a flow restrictor in between two pressure sensors, that form a flow sensor system in total. The flow sensor is connected to safety valve which restricts the flow of the pharmaceutical 50 when the flow sensor system detects an overflow of the pharmaceutical 50. In another example, disclosed in details in U.S. Pat. No. 6,203,523, the flow regulator features a membrane having a hole, the membrane itself positioned above a bottom layer of the reservoir chamber 32 such that sufficient deflection of the membrane causes the membrane to engage against the bottom layer. As liquid flows through the hole a force is applied to the membrane, resulting in a deflection of the membrane which, in turn, impedes the flow path. In a further embodiment the bottom layer features a variable flow channel such that upon membrane deflection flow may only proceed through the hole and through the flow channel. By tailoring the shape and length of the variable flow channel the flow characteristics of the regulator versus pressure may be adjusted. The flow regulator exemplified in this embodiment permits the flow rate to be independent of reservoir pressure within a given pressure range. Other embodiments of the flow regulator 40 suitable for the instant invention are also possible. In certain embodiments, the barrier 30 is a plunger movably installed inside the pressurizable chamber 25. The plunger 30 may be made from a suitably rigid or elastomeric material that preferably is compatible with both the pharmaceutical 50 and the hydraulic fluid 64. That is, the material used to form the plunger 30 is preferably chemically inert with respect to the pharmaceutical 50 and hydraulic fluid 64 so that the material remains structurally sound and does not contaminate the pharmaceutical 50 over the expected shelf-life of the microsyringe 10. Additionally, the plunger 30 should also be able to withstand the temperatures associated with storage of the pharmaceutical 50, such as temperatures of at least −80° C. The plunger 30 may be made, for example, from polypropylene or polyurethane. The shape of the plunger 30 is conformal with the inner surface of the pressurizable chamber 25 to provide a sliding, fluid-tight seal against the inner surface of the pressurizable chamber 25. The inner surface of the pressurizable chamber 25 is preferably smooth and geometrically invariant along the axis along which the plunger 30 is capable of sliding; as shown in FIG. 1, this may be the longitudinal axis of the pressurizable chamber 25. As disclosed above and as a person of the ordinary skill in the art would undoubtedly appreciate, the body 20 does not need to be manufactured as a single, monolithic piece, but can be formed of multiple parts. For example, in one embodiment, the body 20 is formed of two halves, e.g. with the seam running cross-sectionally on the side of the "capsule-shaped" body if, for example, the two halves are threaded and screwed together after the internal components are in place. The plunger 30 fluidly divides the pressurizable chamber 25 into two logically distinct regions: a pharmaceutical reservoir chamber 32 that holds the pharmaceutical 50, and a pressurizable hydraulic fluid chamber 34, which accepts the hydraulic fluid 64 under pressure from the hydraulic fluid delivery system 60. The plunger 30 prevents hydraulic fluid 64 from passing into the pharmaceutical reservoir chamber 32, and similarly prevents the pharmaceutical 50 from leaking out into the pressurizable hydraulic fluid chamber 34. The pharmaceutical reservoir chamber 32 and the pressurizable hydraulic fluid chamber 34 are thus fluidly isolated from each other, though their relative volumes with respect to each other will change as the plunger 30 moves.

A distal face 36 of the plunger 30 is preferably conformal with a proximal face 42 of the flow regulator 40 so that when the plunger 30 abuts the flow regulator 40 a bare minimum of dead space is present so as to minimize waste of the pharmaceutical 50. More generally, when the plunger 30 reaches its most distal stop position, which is as close to the outlet 22 as the plunger 30 can reach, the distal face 36 preferably geometrically conforms to the corresponding shape of the stop position so as to minimize dead space between the distal face 36 and outlet 22. For example, if the flow regulator 40 were instead to be positioned elsewhere along the catheter 24, the distal face 36 of the plunger 30 may have a shape that is conformal to the shape of the distal end (the end containing the outlet 22) of the pressurizable chamber 25.

The catheter 24 is a fluid delivery device, the distal end 29 of which may be positioned into a desired target location within a patient. For example, a pre-positioned guide tube, as known in the art, may be used to position the distal end 29 of the catheter 24 within a patient. Such guide tubes are frequently used, for example, in neurosurgery, and are themselves positioned using stereotactic microdrives. Stereotactic microdrives frequently employ an extremely precise hydraulic system to position the guide tube. Hence, the hydraulic fluid delivery system 60 may be the same hydraulic system that is used by the stereotactic microdrive to position the guide tube. Examples of such a hydraulic systems are the SM-25C Stereotaxic Micromanipulator (Thin-type, Single Axis, Oil Hydraulic System), manufactured by Narishige Co., Ltd., Japan, and the SomaPatch™ MW Series Hydraulic Micromanipulators provided by Soma Scientific Instruments, Irvine, Calif., USA In other embodiments, when the precise location of the targeted area is crucial, e.g., when the pharmaceutical is delivered into the brain of the patient, other mapping means may be used instead of or in addition to the stereotactic positioning. Such mapping means include, without limitation, Positron Emission Tomography and Single Photon Emission Computed Tomography (PET and SPECT, respectively), pharmacological Magnetic Resonance Imaging (ph-MRI), functional MRI (fMRI), and contrast-enhanced computerized tomography (CT) scan. Further, computer-aided atlas-based functional neurosurgery methodology can be used to accurately and precisely inject the pharmaceutical. Such methodologies permit three-dimensional display and real-time manipulation of cerebral structures. Neurosurgical planning with mutually preregistered multiple brain atlases in all three orthogonal orientations is therefore possible and permits increased accuracy of target definition for neurotoxin injection or implantation, reduced time of the surgical procedure by decreasing the number of tracts, and facilitates planning of more sophisticated trajectories. See e.g. Nowinski W. L. et al., Computer-Aided Stereotactic Functional Neurosurgery Enhanced by the Use of the Multiple Brain Atlas Database, IEEE Trans Med Imaging 19(1); 62-69:2000.

Once the guide tube is positioned, the catheter 24 may be fed down the guide tube until the distal end 29 is positioned at the desired location within the patient. To assist in fluoroscopic or x-ray imaging, which may be employed to aid in the positioning of the catheter 24, the catheter 24 may also be provided one or more radiopaque markers, such as at the distal end 29 and at regular intervals between the distal end 29 and the outlet 22. Methods for manufacturing catheters incorporating radiopaque markers are well known in the art, and are disclosed in such issued patents as U.S. Pat. No. 5,846,220 and U.S. Pat. No. 6,179,811, the contents of which are incorporated herein by reference. For example, the radiopaque marker band may be incorporated into the catheter 24 by inserting a mandrel containing the bands of the radiopaque marker into the catheter 24, and then heating the catheter 24 to about 300-350° F. thus melting the bands into the catheter 24. Once distal end 29 is properly positioned, the quick connect/disconnect 62 may be disconnected from the stereotactic microdrive and connected to the corresponding fitting 28 of the inlet 26. In one embodiment, the chamber 34 is pre-packaged with the hydraulic fluid. Similarly, in a preferred embodiment, the chamber 32 is pre-packaged with drug 50. Thus, in such embodiment inlet 26 will also further comprise a seal. In one embodiment, the seal is a foil seal, held onto the end of the device that connects to the hydraulic fluid delivery system by the threaded connection of two portions of the body of the device such that the foil seal is sandwiched between the body of the device and an end-ring. Fluidly connected to the inlet 26, the hydraulic fluid delivery system 60 is then ready to provide hydraulic fluid 64 under finely controlled pressure to the pressurizable hydraulic fluid chamber 34.

For purposes of the instant disclosure, it should be understood that the term "fluid" is broadly meant to include any substance that is capable of flowing and being used as a medium for transferring pressure from one point to another. A fluid may therefore include both gasses and liquids. For example, the hydraulic fluid 64 could, in fact, be nitrogen, filtered air, mineral oil, distilled water, or saline. The pressure provided by the hydraulic fluid delivery system 60 via the hydraulic fluid 64 creates an increase of pressure within the pressurizable hydraulic fluid chamber 34. This increased pressure exerts a force upon the plunger 30, causing the plunger 30 to slide distally towards the outlet 22. The distal movement of the plunger 30 causes a corresponding volumetric displacement of the pharmaceutical 50, which flows past the flow regulator 40, through the catheter 24 and into the patient at the predetermined position set by the distal end 29 of catheter 24. By utilizing the hydraulic fluid delivery system 60 to finely control the pressure developed in the pressurizable hydraulic fluid chamber 34, precise control of the delivery rate of the pharmaceutical 50 is made possible over extended periods of time; however, in no event will the delivery rate exceed the maximum rate set by the flow regulator 40, thus ensuring patient safety. In the preferred embodiment, regulator 40 will allow a single maximum flow rate that is equal to the desired flow rate, and any minimal externally applied pressure by hydraulic fluid system 60 is sufficient to deliver the pharmaceutical 50 (e.g., viral particles) from body 20 through the flow regulator 40 and to the patient at that desired flow rate. Because the entire body 20 will experience the delivery pressure exerted by the hydraulic fluid delivery system 60, it is desirable that the body 20 be fashioned to withstand at least the maximum pressures expected from the hydraulic delivery system 60. Assuming that the maximum pressure will be about 80 mm Hg, the body 20 is preferably made of polypropylene of having a minimum thickness of about 1 mm. Since the cannula is preferably made of a metal, such as, for example, stainless steel, no special considerations are needed for the metal to be able to withstand the pressure ranging up to 80 mm Hg.

Exemplary manufacturing steps for microsyringe 10 are: 1) the body 20 is molded in two threaded halves, 2) the cannula 24 is attached to the end of body 20 by, for example, a threaded connection, 3) the distal end of body 20 and the entire cannula 24 are filled with the viral vector and frozen, 4) the plunger 30 is placed on top of the frozen vector and the second half of the body 20 is attached by a threaded connection, 5) the second half of the body 20 is filled with mineral oil, 6) a cap with a foil seal is placed at the open end of the second half of body 20 and attached by a ring with a threaded connection, 7) the entire unit is placed in a sterile outer packaging, and sterilized by exposure to ethylene oxide gas. Once completed, the pre-packaged microsyringe 10 may be transported and stored under temperatures that are suitable to ensure preservation of the pharmaceutical 50. When pharmaceutical 50 is needed, the microsyringe 10 may be taken from storage and provided to the physician, who removes the microsyringe 10 from its sterile packaging and uses the microsyringe 10 in conjunction with the hydraulic fluid delivery system 60 to administer the pharmaceutical 50, as described above. After the pharmaceutical 50 has been administered, the microsyringe 10 may be discarded. The microsyringe 10 thus provides a single-use cartridge that may be conveniently delivered into the operating room when needed.

The microsyringe of the instant invention can be used to deliver different pharmaceuticals. Suitable examples include small molecules, such as, for example, ibuprofen, and proteins or fragments thereof, including, for example, glial cell derived neurotrophic factor, or GDNF. In addition, the microsyringe can be used to deliver gene therapy systems, whether administered as naked nucleic acid sequences or within vectors, including both viral and non-viral vectors, providing suitable dosages of these pharmaceuticals into the operating room as needed with minimal waste.

A second embodiment of microsyringe 200 is shown in FIG. 2. As in the prior embodiments, the microsyringe 200 comprises a body 220, a barrier 230 and a flow regulator 240. The body 220 defines a pressurizable chamber 225 having an inlet 226 and an outlet 222. The inlet 226 and outlet 222 are both fluidly connected to the pressurizable chamber 225. Inlet 226 includes quick connect/disconnect fitting 228 that is designed to mechanically and fluidly couple to quick connect/disconnect mating 62 of hydraulic fluid delivery system 60.

The body 220 also defines cannula 224 that is fluidly connected to the outlet 222. The primary difference between this embodiment and those described above is that the barrier 230 is a collapsible membrane disposed inside the pressurizable chamber 225 and fluidly connected to the outlet 222 via the flow regulator 240. The collapsible membrane 230 is used to hold pharmaceutical 250, and is preferably pre-filled with pharmaceutical 250 prior to shipping of the microsyringe 200.

The collapsible membrane 230 may be made from any suitably flexible or easily deformable material, either by design through shape, inherently by material properties or both, and is preferably compatible with the pharmaceutical 250 and the hydraulic fluid 64. Additionally, the collapsible membrane is preferably able to withstand the storage temperatures associated with the pharmaceutical 250, such as such as temperatures of −80° C. or lower. The collapsible membrane 230 may be made, for example, from a thermoplastic hydrocarbon elastomer, such as thermoplastic polyolefin elastomer. Methods for manufacturing a pharmaceutical delivery device comprising an internal, collapsible membrane, are well known in the art and exemplified by U.S. Pat. No. 4,203,440, incorporated herein by reference in its entirety. The device disclosed in U.S. Pat. No. 4,203,440 differs from the microsyringe of the instant invention in that the expulsion of the pharmaceutical 50 from within microsyringe 200 occurs due to the increase in hydraulic pressure in chamber 225, rather than due to influx of fluid into an outer chamber due to osmosis as disclosed in U.S. Pat. No. 4,203,440. The collapsible membrane 230 fluidly divides the pressurizable chamber 225 into two logically distinct regions: a pharmaceutical reservoir chamber 232 that holds the pharmaceutical 250, and a pressurizable hydraulic fluid chamber 234, which accepts the hydraulic fluid 64 under pressure from the hydraulic fluid delivery system 60. The collapsible membrane 230 is ideally impermeable to both the pharmaceutical 250 and the hydraulic fluid 64. The pharmaceutical reservoir chamber 232 and the pressurizable hydraulic fluid chamber 234 are therefore fluidly isolated from each other, although fluidly connected to outlet 222 and inlet 226, respectively.

Once connected to fitting 228, the hydraulic fluid delivery system 60 creates an increase of pressure within the pressurizable hydraulic fluid chamber 234. This pressure exerts a force upon the collapsible membrane 230, in effect squeezing the pharmaceutical 250 out of the pharmaceutical reservoir chamber 232. The pharmaceutical 250 flows past the flow regulator 240 and outlet 222, through the cannula 224 and into the patient at the predetermined position set by the distal end 229 of cannula 224. The fine pressure control provided by the hydraulic fluid delivery system 60 enables precise control of the delivery rate of the pharmaceutical 250 over extended periods of time. Flow regulator 240 ensures that the flow rate of pharmaceutical 250 through cannula 224 never exceeds the pre-set maximum rate. The body 220 is preferably fashioned to withstand at least the maximum pressures expected from the hydraulic delivery system 60 to avoid unexpected structural failures of any portion of the body 220. It will be appreciated that hydraulic fitting 228 may comprise a one-way valve to prevent backflow of the hydraulic fluid 64 from the pressurizable hydraulic fluid chamber 234.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A microsyringe comprising:
a pharmaceutical reservoir chamber;
a pressurizable hydraulic fluid chamber;
a barrier moveably disposed between the pharmaceutical reservoir chamber and the pressurizable hydraulic fluid chamber, the barrier fluidly isolating the pharmaceutical reservoir chamber from the pressurizable hydraulic fluid chamber;
an inlet fluidly connected to the pressurizable hydraulic fluid chamber, the inlet comprising a fitting to mechanically and fluidly connect to a corresponding mating of a hydraulic fluid delivery system to provide hydraulic fluid to the pressurizable hydraulic fluid chamber, the inlet providing hydraulic fluid to the pressurizable hydraulic fluid chamber without loss of pressure;
a single flow regulator directly and fluidly connected to the pharmaceutical reservoir chamber and configured to prevent a delivery rate of a pharmaceutical in the pharmaceutical reservoir chamber from exceeding a predetermined maximum rate; and
a cannula connected to the flow regulator.

2. The microsyringe of claim 1 wherein the pharmaceutical reservoir chamber is pre-filled with the pharmaceutical.

3. The microsyringe of claim 1 wherein the barrier is a plunger slidably disposed between the pharmaceutical reservoir chamber and the pressurizable hydraulic fluid chamber.

4. The microsyringe of claim 1 wherein the barrier is a collapsible membrane.

5. A microsyringe comprising:
a body comprising:
a pressurizable chamber;
an inlet fluidly connected to the pressurizable chamber and comprising a fitting to mechanically and fluidly connect to a corresponding mating of a hydraulic fluid delivery system, the inlet providing hydraulic fluid to the pressurizable hydraulic fluid chamber without loss of pressure;
an outlet fluidly connected to the pressurizable chamber; and
a cannula fluidly connected to the outlet;
a barrier movably disposed within the pressurizable chamber and fluidly separating the inlet from the outlet; and
a single flow regulator directly connected to the cannula and configured to prevent a delivery rate of a pharmaceutical flowing through the cannula from exceeding a predetermined maximum rate.

6. The microsyringe of claim 5 wherein a pharmaceutical reservoir chamber extending between the barrier and the outlet is pre-filled with the pharmaceutical.

7. The microsyringe of claim 5 wherein the barrier is a plunger slidably disposed in the pressurizable chamber.

8. The microsyringe of claim 5 wherein the barrier is a collapsible membrane.

9. The microsyringe of claim 5 wherein the body is made of a material capable of withstanding temperatures of at least −80° C.

10. The microsyringe of claim 5 wherein the cannula is a catheter.

11. The microsyringe of claim 1 or 5, wherein the pharmaceutical comprises a gene therapy system.

12. A method of delivering a pharmaceutical to a desired target location within a patient comprising:
locating the desired target location;

placing a distal tip of the microsyringe of either claim 1 or claim 5 into a position allowing a direct access to the desired target location, wherein the microsyringe contains the pharmaceutical; and releasing the pharmaceutical.

13. The method of claim 12, wherein the desired target location is within a brain of the patient.

14. The microsyringe of claim 1 wherein the flow regulator fluidly prevents the delivery rate of the pharmaceutical from exceeding 5.0 microliters per minute.

15. The microsyringe of claim 5 wherein the flow regulator fluidly prevents the delivery rate of the pharmaceutical from exceeding 5.0 microliters per minute.

16. The microsyringe of claim 1 further comprising a seal covering the inlet.

17. The microsyringe of claim 5 further comprising a seal covering the inlet.

* * * * *